US011488694B2

(12) United States Patent
Malone et al.

(10) Patent No.: US 11,488,694 B2
(45) Date of Patent: Nov. 1, 2022

(54) METHOD AND SYSTEM FOR PREDICTING PATIENT OUTCOMES USING MULTI-MODAL INPUT WITH MISSING DATA MODALITIES

(71) Applicant: NEC Laboratories Europe GmbH, Heidelberg (DE)

(72) Inventors: Brandon Malone, Dossenheim, DE (US); Mathias Niepert, Heidelberg (DE); Alberto Garcia Duran, Heidelberg (DE); Maja Schwarz, Heidelberg (DE)

(73) Assignee: NEC CORPORATION, Tokyo (JP)

( * ) Notice: Subject to any disclaimer, the term of this patent is extended or adjusted under 35 U.S.C. 154(b) by 487 days.

(21) Appl. No.: 16/293,706

(22) Filed: Mar. 6, 2019

(65) Prior Publication Data

US 2019/0325995 A1    Oct. 24, 2019

Related U.S. Application Data

(60) Provisional application No. 62/660,294, filed on Apr. 20, 2018.

(51) Int. Cl.
*G16H 10/60* (2018.01)
*G06N 20/00* (2019.01)
*G06N 5/02* (2006.01)
*G16H 40/20* (2018.01)

(52) U.S. Cl.
CPC .............. *G16H 10/60* (2018.01); *G06N 5/02* (2013.01); *G06N 20/00* (2019.01); *G16H 40/20* (2018.01)

(58) Field of Classification Search
CPC .......... G16H 10/60; G06N 20/00; G06N 5/02
See application file for complete search history.

(56) References Cited

U.S. PATENT DOCUMENTS

| 2004/0128168 A1* | 7/2004 | Wyatt | G06Q 10/087 705/2 |
| 2013/0018830 A1* | 1/2013 | Dhurandhar | G06N 7/005 706/14 |

(Continued)

OTHER PUBLICATIONS

Tooth et al, "Length of Stay, Discharge Destination, and Functional Improvement", Jul. 2005, Stroke Journal, pp. 1519-1525 (Year: 2005).*

(Continued)

*Primary Examiner* — Jonathan Durant
*Assistant Examiner* — Anne-Marie K Alderson
(74) *Attorney, Agent, or Firm* — Leydig, Voit & Mayer, Ltd.

(57) ABSTRACT

A method for predicting a patient outcome from a caretaker episode includes receiving a current episode snapshot of the caretaker episode comprising multi-modal data of the patient from an electronic health records (EHR) system, the multi-modal data including one or more available data modalities and one or more missing data modalities. The multi-modal data is applied as input to an embedding model having a submodel for each of the data modalities. A first embedding is generated for each of the available data modalities. A second embedding is generated for each of the missing data modalities using corresponding embeddings of neighbors in an episode snapshot graph. The first and second embeddings are combined to obtain a complete embedding. The patient outcome is predicted based on the complete embedding for the current episode snapshot using a machine learning component which has been trained using patient outcomes of the historical episode snapshots.

15 Claims, 7 Drawing Sheets

(56) References Cited

U.S. PATENT DOCUMENTS

| | | | | |
|---|---|---|---|---|
| 2014/0108033 A1* | 4/2014 | Akbay | ............ | G06F 19/00 |
| | | | | 705/2 |
| 2014/0310218 A1* | 10/2014 | Min | ............ | G06N 3/08 |
| | | | | 706/16 |
| 2016/0063212 A1* | 3/2016 | Monier | ............ | G16H 50/50 |
| | | | | 705/3 |
| 2016/0125152 A1* | 5/2016 | Higgs | ............ | G06F 19/3418 |
| | | | | 705/3 |
| 2017/0249434 A1* | 8/2017 | Brunner | ............ | G06F 19/3418 |
| 2019/0034590 A1* | 1/2019 | Oren | ............ | G06N 3/08 |

OTHER PUBLICATIONS

Stecker et al, "Predictive model of length of stay and discharge destination in neuroscience admissions", Feb. 6, 2017, Surg Neurol Int 2017;8:17. (Year: 2017).*

Wikipedia, "Deep Learning" page, https://en.wikipedia.org/wiki/Deep_learning, accessed Mar. 16, 2018 (Year: 2018).*

Barnes et al., "Real-Time Prediction of Inpatient Length of Stay for Discharge Prioritization," *J Am Med Inform Assoc*, 23: e2-e10 (Aug. 2016).

Lipton et al., "Modeling Missing Data in Cinical Time Series with RNNs," *JMLR W&C*, 56 (Dec. 2016).

Marlin, et al., "Unsupervised Pattern Discovery in Electronic Health Care Data Using Probabilistic Clustering Models," *Proceedings of the $2^{nd}$ ACM SIGHIT International Health Informatics Symposium*: 389-398 (Jan. 28-30, 2012).

Stecker, et al., "Predictive Model of Length of Stay and Discharge Destination in Neurosciene Admissions," *Surg Neurol Int*, 8 (17) (Feb. 6, 2017).

Garcia-Duran, et al., "Learning Graph Representations with Embedding Propagation," $31^{st}$ *Conference on Neural Information Processing Systems*: 1-12 (Oct. 9, 2017).

* cited by examiner

METHOD AND SYSTEM FOR PREDICTING PATIENT OUTCOMES USING MULTI-MODAL INPUT WITH MISSING DATA MODALITIES

CROSS-REFERENCE TO PRIOR APPLICATION

Priority is claimed to U.S. Provisional Application No. 62/660,294 filed on Apr. 20, 2018, the entire contents of which is hereby incorporated by reference herein.

FIELD

The present invention relates to a method and system for predicting patient outcomes from a given caretaker episode using multi-modal raw patient data as input, wherein data modalities are missing. The predictions are useable for resource management and to manage and plan for patient discharge from the episode.

BACKGROUND

Healthcare is an integral service in modern societies. However, improving its quality and efficiency through technology has often proven to be challenging and costly. For example, even though electronic health records (EHRs) provide a wealth of information carrying the potential to improve treatment quality and patient outcomes, extracting useful and actionable medical insights from EHRs poses several technological challenges both to traditional statistical and machine learning techniques. First, not all patients receive the same set of laboratory tests, examinations, consultations, etc., while they are at the hospital. Thus, many patients have missing, incomplete and non-standardized data relative to other patients. Second, the various medical conditions and the corresponding treatment activities yield different kinds of data. For example, a blood oxygen saturation sensor may collect numeric values for a given amount of time at a fixed frequency, while a consultation with a physician may produce only free text notes of the physician's interpretation. Thus, there are multiple modalities of data and these modalities have variations due to a number of external factors. Third, patients may share important relationships which are not easily captured in typical data representations. For example, family members often share a similar genetic background. Likewise, patients with similar initial diagnoses may share underlying characteristics which are difficult to capture in traditional models. Thus, it is a challenge to detect the relationships among patients and explicitly model the relationships that capture some form of disease or treatment affinity.

The foregoing challenges make it difficult to effectively utilize EHRs to improve healthcare services, for example, to better predict patient outcomes. Accurate predictions of patient outcomes can be used for more effective daily operation of healthcare providers and the healthcare system in general. After an initial admission to a hospital, these outcomes could be expressed and predicted as the length of stay (LOS) in hospital, discharge destination (DD) or a multitude of scores that reflect the recovery rate. For instance, after a stroke the patient recovery can be measured by the functional independence measure (FIM) score consisting of eighteen physical, psychological and social items.

Predictions of patient outcomes can be used for more efficient resource allocation. For example, the expected LOS is used for planning purposes in intensive care units (ICUs). In cases where the expected LOS of already-admitted patients changes, it is possible that the unit would require an allocation of additional beds and nurses. Similarly, knowing a patient's DD early enough also allows for better planning at the DDs. Studies show that patients are often required to stay longer in hospitals since rehab centers do not receive prior notice and are not ready to receive them. Likewise, a patient might be required to stay longer in the hospital, if family of the patient had not been notified early enough that the patient will be discharged home. For example, if not notified early enough, the family may not have enough time to organize the necessary additional help or equipment such as a special bed and a wheelchair. All of these factors, among others, contribute to extending the average LOS and thereby incurring unnecessary costs to the healthcare system.

Existing applications of machine learning in the healthcare domain have attempted to address the problem of multivariate time series measurements. However, such works are limited to the time series measurements as a single data modality for prediction and are not able to utilize or learn on multi-modal data to make predictions of patient outcomes. Other works using discrete observations, such as prescribed medications or International Classification of Diseases (ICD) codes assigned during billing, do not capture similarity relationships between patients and do not consider the impact of missing data.

SUMMARY

In an embodiment, the present invention provides a method for predicting a patient outcome from a caretaker episode. The method includes receiving a current episode snapshot of the caretaker episode comprising multi-modal data of the patient from an electronic health records (EHR) system, the multi-modal data including one or more available data modalities and one or more missing data modalities. The multi-modal data is applied as input to an embedding model having a submodel for each of the data modalities. A first embedding is generated for each of the available data modalities using a respective one of the submodels. A second embedding is generated for each of the missing data modalities using corresponding embeddings of neighbors in an episode snapshot graph which connects the current episode snapshot to other historical episode snapshots based on a similarity measure. The first and second embeddings are combined to obtain a complete embedding for the current episode snapshot. The patient outcome is predicted based on the complete embedding for the current episode snapshot using a machine learning component which has been trained using patient outcomes of the historical episode snapshots.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
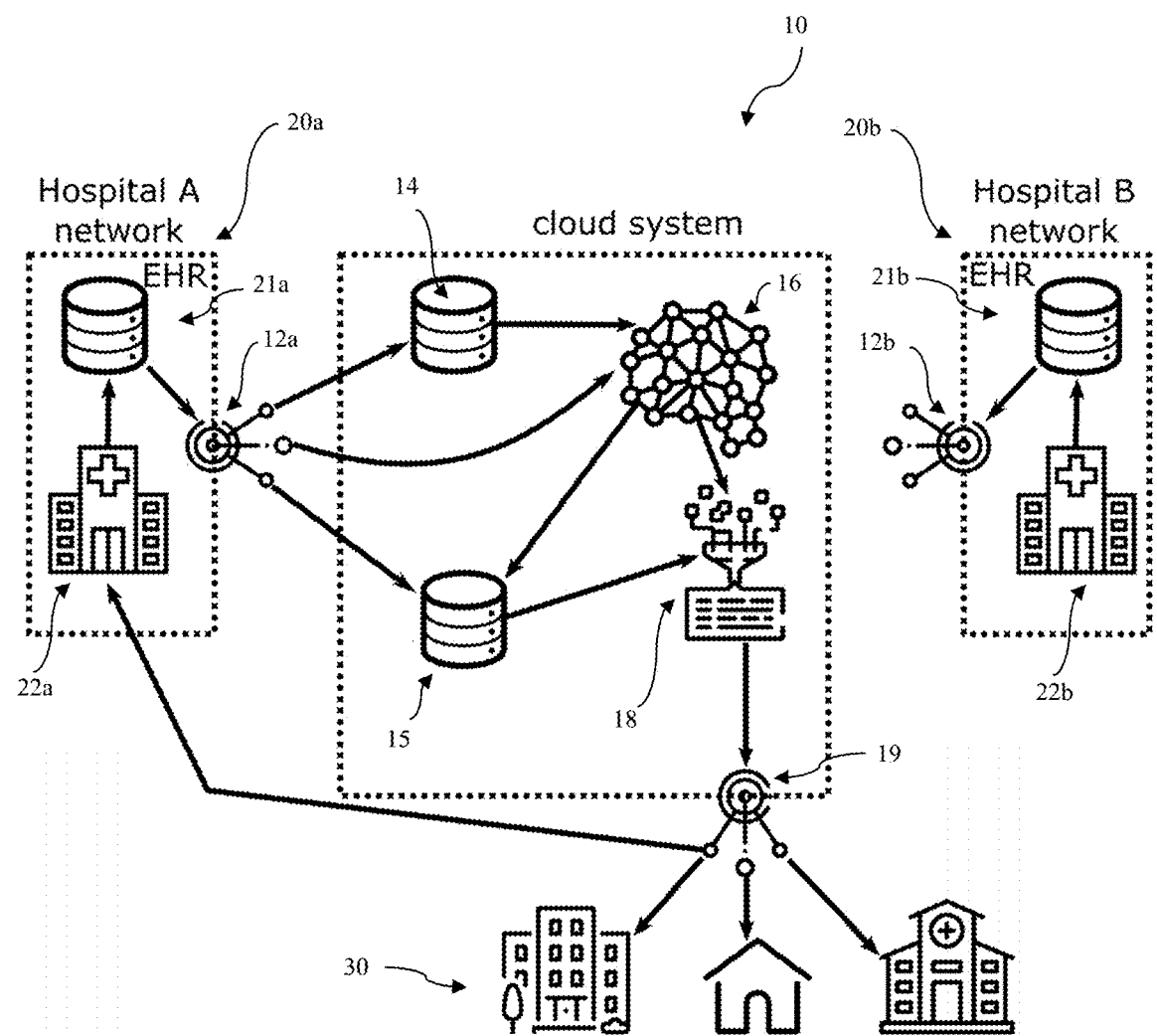
FIG. 1 schematically illustrates a cloud-based system and method for predicting patient outcomes according to embodiments of the present invention.

Embodiments of the present invention provide a method and a system for handling patient discharges from a given caretaker episode, such as an admission into an ICU. An "episode" refers to a patient visit at the caretaker, such as a stay in the ICU. According to embodiments of the system and method, machine learning models are used to estimate descriptions of discharge, including the time of discharge and DD using multi-modal and missing data generated during episodes of other patients and extracted from EHRs. The method uses patient data, such as results of laboratory tests and physicians notes, to accurately predict when and/or to where a given patient will be discharged. Advantageously, the method uses the multi-modal data to enhance accuracy and can determine embeddings for the missing data embeddings, which also enhances accuracy. This method allows hospitals to accurately estimate future strains on capacity and reallocate resources accordingly. Further, the method permits coordination between the hospital and external facilities, such as rehabilitation clinics, to optimize patient discharges to the external facilities. Compared to existing approaches, embodiments of the present invention improve patient outcomes through the more timely and accurate predictions thereof. For example, it is possible to reduce patient discomfort when transferring by ensuring their arrival is expected at the destination. Likewise, embodiments of the present invention allow informed decision-making for resource allocation within the hospitals and external facilities. Thus, decision makers can improve efficiency by, for example, ensuring enough free beds are available for the expected patient load. Moreover, the method enhances privacy of patient data by utilizing learned embeddings.

While experienced physicians are able to make their own estimates of patient outcomes based on their years of experience, these physicians are already overburdened providing primary care to patients. Moreover, such an approach is not standardized and often inaccurate. According to an embodiment of the present invention, in contrast, the approach is standardized and highly accurate, and allows that predictions could be done by other persons, such as nurses and hospital operational staff, using a computer network based information technology (IT) system. In this way, additional burden could be moved away from already busy physicians and the IT system can be used directly in standardized hospital workflows as an automated process by caretakers who lack years of experience. Embodiments of the present invention provide the IT system utilizing prediction models that take patient data as input and predict relevant patient outcomes to improve patient care and inform resource allocation decisions. The system can integrate directly into standardized hospital workflows.

According to an embodiment, the present invention provides a networked computer system which collects relevant data from existing EHR systems and predicts the relevant patient outcomes, such as the remaining LOS of an episode as well as the DD. Additionally, feedback about the actual LOSs and DDs can be given to the system for improved performance later. According to another embodiment, the predictions of patient outcomes could be used when designing a therapeutic plan, for example, by helping to determine the necessary number of rehab sessions. According to a further embodiment, the predictions could be used to identify patients that need to be prioritized and receive more care. All components of the system according to embodiments of the present invention communicate over secure channels.

One particular advantage of the system according to an embodiment of the present invention is the system's ability to account for multiple modalities of data (including, e.g., demographics, notes from physicians, readouts from sensors, laboratory results, etc.), where some of the modalities are missing, to predict the relevant patient outcomes, such as LOS and DD of an episode. Advantageously, the predictions can also be updated during the episode. Accordingly, relevant data about the episode can be acquired throughout the episode. As used herein, an "episode snapshot" refers to the observations during an episode so far and a time span between the beginning of the episode and a current time.

In providing to use multiple data modalities for the predictions for increased accuracy, embodiments of the present invention solve the technical challenge of how to use the multiple data modalities despite some of the data modalities being missing, as can typically be the case. According to embodiments of the present invention, meaningful embeddings of missing data are determined by combining observations from similar episodes. As data becomes available for the current episode, the determined embeddings are updated. Embeddings are dense numeric vectors, and can sometimes be also referred to as representations or summaries.

In an embodiment, the present invention provides a method for predicting a patient outcome from a caretaker episode. The method includes receiving a current episode snapshot of the caretaker episode comprising multi-modal data of the patient from an electronic health records (EHR) system, the multi-modal data including one or more available data modalities and one or more missing data modalities. The multi-modal data is applied as input to an embedding model having a submodel for each of the data modalities. A first embedding is generated for each of the available data modalities using a respective one of the submodels. A second embedding is generated for each of the missing data modalities using corresponding embeddings of neighbors in an episode snapshot graph which connects the current episode snapshot to other historical episode snapshots based on a similarity measure. The first and second embeddings are combined to obtain a complete embedding for the current episode snapshot. The patient outcome is predicted based on the complete embedding for the current episode snapshot using a machine learning component which has been trained using patient outcomes of the historical episode snapshots.

In the same or other embodiment, the patient outcome includes a remaining length of stay (LOS) and a discharge destination (DD), wherein the DD is predicted using the predicted LOS.

In the same or other embodiment, the method further comprises alerting the predicted DD of the predicted patient outcome.

In the same or other embodiment, the remaining LOS prediction is made by combining predictions at different levels of granularity including a first prediction at a finer granularity made using a regression model and at least one second prediction at a coarser granularity made using an ordinal regression or classification model.

In the same or other embodiment, the embedding model is an unsupervised embedding model trained based on the historical episode snapshots.

In the same or other embodiment, the machine learning component includes a supervised machine learning model trained to predict the patient outcome based on embeddings of the episode snapshots and outcomes of the historical episode snapshots.

In the same or other embodiment, each of the submodels of the embedding model is a one-way function whose parameters are learned with a contrastive loss function comparing an embedding of a respective one of the data modalities, accounting for observed and missing values, with an aggregated embedding of embeddings of the respective one of the data modalities from the neighbors in the episode snapshot graph.

In the same or other embodiment, the multi-modal data originates from different EHR systems.

In the same or other embodiment, the multi-modal data includes at least time series measurements, free text notes and demographic information.

In another embodiment, the present invention provides a system for predicting a patient outcome from a caretaker episode. The system includes at least one server operable to receive patient raw data for the caretaker episode from at least one electronic health records (EHR) system, the at least one server having memory and one or more computational processors which, alone or in combination, are configured to provide for execution of a method comprising: receiving a current episode snapshot of the caretaker episode comprising multi-modal data of the patient from the at least one EHR system, the multi-modal data including one or more available data modalities and one or more missing data modalities; applying the multi-modal data as input to an embedding model having a submodel for each of the data modalities; generating a first embedding for each of the available data modalities using a respective one of the submodels; generating a second embedding for each of the missing data modalities using corresponding embeddings of neighbors in an episode snapshot graph which connects the current episode snapshot to other historical episode snapshots based on a similarity measure; combining the first and second embeddings to obtain a complete embedding for the current episode snapshot; and predicting the patient outcome based on the complete embedding for the current episode snapshot using a machine learning component which has been trained using patient outcomes of the historical episode snapshots In the same or other embodiment, the at least one server is located in the Cloud and is configured to receive the patient raw data from different EHR systems by secure communication with respective communication interfaces within the different EHR systems.

In the same or other embodiment, the at least one server is embedded within the at least one EHR system.

In the same or other embodiment, the system further comprises an episode snapshot database storing at least a portion of the episode snapshots, and an episode embedding database storing the complete embeddings of at least a portion of the episode snapshots and at least a portion of known outcomes of the episode snapshots.

In the same or other embodiment, the patient outcome includes a remaining length of stay (LOS) and a discharge destination (DD), and the system further comprises a notification communication system configured to alert the predicted DD about the predicted patient outcome.

In a further embodiment, the present invention provides a tangible, non-transitory computer-readable medium having instructions thereon which, upon execution by one or more processors with memory, provide for execution of a method comprising: receiving a current episode snapshot of the caretaker episode comprising multi-modal data of the patient from an electronic health records (EHR) system, the multi-modal data including one or more available data modalities and one or more missing data modalities; applying the multi-modal data as input to an embedding model having a submodel for each of the data modalities; generating a first embedding for each of the available data modalities using a respective one of the submodels; generating a second embedding for each of the missing data modalities using corresponding embeddings of neighbors in an episode snapshot graph which connects the current episode snapshot to other historical episode snapshots based on a similarity measure; combining the first and second embeddings to obtain a complete embedding for the current episode snapshot; and predicting the patient outcome based on the complete embedding for the current episode snapshot using a machine learning component which has been trained using patient outcomes of the historical episode snapshots.

According to a first embodiment schematically illustrated in FIG. 1, the system is a cloud-based system 10 which is able to integrate data from multiple caretakers. The cloud-based system 10 communicates with communication interfaces 12a, 12b located at different hospital networks 20a, 20b of different hospitals 22a, 22b. The communication interfaces 12a, 12b are used to extract episode snapshots from the respective EHR systems 21a, 21b of the respective hospital networks 20a, 20b for use by the cloud-based system 10. The cloud-based system 10 includes an episode snapshot database 14 which stores sensitive patient information received from the respective EHR systems 21a, 21b via the respective communication interfaces 12a, 12b, as well as an episode embedding database 15 which stores privacy-preserving embeddings of episode snapshots, as well as their outcomes (LOS and DD), when available. The cloud-based system 10 further includes an embedding model 16 which combines observed episode data with those from similar episodes to account for missing data in order to create an embedding of the episode snapshot, as well as a machine learning component 18 which predicts both the remaining duration of the episode and the discharge destination using the embedding of the episode snapshot. The cloud-based system 10 can further include a notification communication system 19 to alert, for example, the DDs 30, of predicted upcoming patient arrivals. The DDs 30 preferably have or provide a secure communication interface and address for communication. Lightweight approaches, such as email or text messages, can be used by the notification communication system 19 for alerting the DDs 30.

The communication interfaces 12a, 12b in each case extract raw data stored in a secure database of their respective EHR systems 21a, 21b and securely transfer the raw data to the embedding model 16. The communication interfaces 12a, 12b extract many modalities of input data which are available in the secure databases of the EHR systems 21a, 21b for each episode, including, e.g., patient demographics, text notes (e.g., like those often made after radiology screenings), administered laboratory tests and their results, time series measurements from sensors (e.g., blood oxygen saturation monitors), prescribed medications, and applied treatments (e.g., physical therapy). In order to ensure data privacy and secure communication between the cloud-based system 10 the EHR systems 21a, 21b, the extraction takes place inside the respective hospital computing networks 20a, 20b (e.g., using a processor connected to the secure databases of the EHR systems 21a, 21b) and the extracted data is sent to one or more servers of the cloud-based system 10 via an encrypted communication channel.

According to an embodiment, the cloud-based system 10 considers three levels of data permission from the patient:

High permission: In this case, the complete episode snapshots (i.e., raw patient data), including outcomes (once available), are stored in the episode snapshot database 14. In this setting, the communication interfaces 12a, 12b communicate directly with the episode snapshot database 14 as new data for a patient becomes available. The communication includes an "episode identifier" to uniquely identify all snapshots for a particular episode.

Low permission: In this case, the embeddings of the episode snapshots, as well as outcomes (once available), are stored in the episode embedding database 15. Raw patient data is not stored in this case in the episode snapshot database 14. For this level of permission, the communication interfaces 12a, 12b send episode snapshots (including an episode identifier as in the high permission setting) directly to the embedding model 16 for processing. When the outcomes become available, the communication interfaces 12a, 12b send them (and the episode identifier) to the episode embedding database 15.

No permission: For patients with no level of permission, no information will be stored. The episode snapshots (without any episode identifier) are sent directly to the embedding model 16 for processing. The communication interfaces 12a, 12b do not extract the outcomes for these episodes, and they are not used in any kind of downstream machine learning training.

For all permission settings, the raw patient data is normalized to a standard representation using, for example, the standard Fast Healthcare Interoperability Resources format. This ensures that data from multiple caretaker is interoperable.

Naive examples of several transfers for the same episode are as follows:

SNAPSHOT 1
  episode_identifier: 8675309
  time_span: 00:00:00
  gender: male
  age: 50
  initial_diagnosis: "CORONARY ARTERY DISEASE\ CORONARY ARTERY BYPASS GRAFT"
  current_medications: aspirin
SNAPSHOT 2
  episode_identifier: 8675309
  time_span: 00:00:00
  gender: male
  age: 50
  initial_diagnosis: "CORONARY ARTERY DISEASE\ CORONARY ARTERY BYPASS GRAFT"
  current_medications: aspirin
  time_span: 00:30:00
  intra-arterial_systolic_blood_pressure: 135
  heart_rate: 110
  treatment: anesthetic
SNAPSHOT 3
  episode_identifier: 8675309
  time_span: 00:00:00
  gender: male
  age: 50
  initial_diagnosis: "CORONARY ARTERY DISEASE\ CORONARY ARTERY BYPASS GRAFT"
  current_medications: aspirin
  time_span: 00:30:00
  intra-arterial_systolic_blood_pressure: 135
  heart_rate: 110
  treatment: anesthetic
  time_span: 00:30:05
  intra-arterial_systolic_blood_pressure: 130
  arterial_oxygen: 70 mmHg
SNAPSHOT 4
  episode_identifier: 8675309
  time_span: 00:00:00
  gender: male
  age: 50
  initial_diagnosis: "CORONARY ARTERY DISEASE\ CORONARY ARTERY BYPASS GRAFT"
  current_medications: aspirin
  time_span: 00:30:00
  intra-arterial_systolic_blood_pressure: 135
  heart_rate: 110
  treatment: anesthetic
  time_span: 00:30:05
  intra-arterial_systolic_blood_pressure: 130
  arterial_oxygen: 70 mmHg
  time_span: 57:30:05
  discharge_destination: Nursing Facility ABC The extracted and normalized data are forwarded to the appropriate components in the cloud system based on the permissions determined by each patient. All communication occurs over an encrypted communication channel in order to preserve patient privacy.

Regardless of the security choice of the patient, each snapshot would always be sent to the embedding model 16 according to an embodiment. The embedding model would create an embedding and then use the machine learning component 18 to predict the outcomes for the episode.

In the case of low or high permission, each episode snapshot embedding and episode identifier are stored in the episode embedding database 15. The episode_identifer, discharge_destination, and its associated time_span are also saved in the episode embedding database 15 according to an embodiment. Thus, according to an embodiment, episode embedding database 15 stores embeddings of episode snapshots (computed by the embedding model 16), as well as the LOS of the episode at the time of the snapshot, and the outcomes (total LOS of the episode and the DD) when known. As described in more detail below, this data is used to train the machine learning component 18.

In the case that the patient chose high permission, then all snapshots would be transferred to and stored in the episode snapshot database 14. The episode snapshot database 14 stores all raw patient data and modalities, including demographics, lab results, notes, etc., for patients who allow high permission. The format of the episode snapshot database 14 can be, for example, a relational database, such as SQL-Server, a No-SQL database, such as Redis, or any other appropriate format. As described in more detail below, this data is used to train the embedding model 16.

The embedding model 16 transforms the disparate data modalities of the episode snapshots as the input data into a common embedding. Specifically, the embedding model 16 contains one submodel for each data modality. Each submodel is a function with a set of parameters which takes as input the respective data modality and outputs dense numeric vectors as the common embedding. A unified embedding of each episode is then constructed by combining the common embeddings of each modality. The unified embedding is then created for the new episode as before. The embedding model 16 contains an "episode snapshot graph" which connects similar episode snapshots stored in the episode snapshot database 14.

According to an embodiment of the present invention, expert knowledge is used to define a similarity among episode snapshots based on the raw data. For example, the status of the patient at the time of admission could be used to calculate a similarity. In a specific embodiment, the similarity can be determined in accordance with Equation 6 below. The episode snapshot graph is then created by connecting the most similar episode snapshots. According to an embodiment, embeddings are not used to create the episode snapshot graph.

Figure 2:
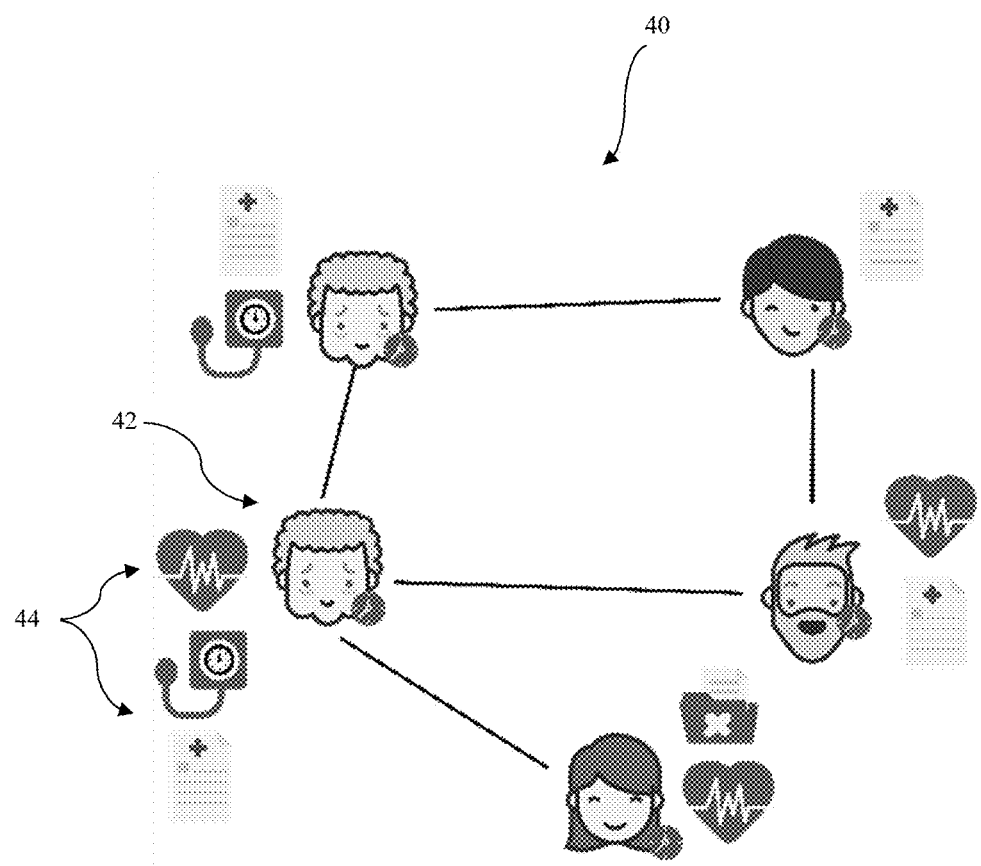
FIG. 2 shows an example of an episode snapshot graph with each node representing an episode snapshot.

FIG. 2 schematically shows an example of an episode snapshot graph 40 in which the nodes represent distinct episode snapshots 42 of different patients each having one or more available data modalities 44 represented by the icons beside each of the nodes. For at least some of the episode snapshots 42 there are missing data modalities 44. In the example of FIG. 2, there are multiple episode snapshots from the same episode (represented on the left side of FIG. 2 by the two nodes having the same "grandmother" icon). The nodes also store the LOS of the episode at the time of the episode snapshot 42 represented by the clock icons at each of the nodes.

The episode snapshot graph 40 is used for two purposes. First, the parameters of each submodel are learned such that connected episode snapshots 42 have similar embeddings. Second, the episode snapshot graph 40 is used to construct embeddings for missing data modalities 44 as follows: When a new episode snapshot is observed, its neighborhood is located in the episode snapshot graph by using the previously-described similarity measure. Then, the episode snapshots 42 which are neighbors to the new episode snapshot pass messages to the new episode snapshot in order to construct an embedding for each of its missing data modalities. In a specific embodiment, the embeddings of the observed data are calculated in accordance with Equation 1 below, and the embeddings for (partially) missing data are calculated in accordance with Equation 2, wherein the messages are the $f_i(x)$ terms in Equation 2. Further, the messages allow embedding construction for partially observed modalities. For example, an EHR may contain the gender and ethnicity for the patient associated with an episode snapshot 42, but not that patient's age. The messages from the neighbors allow embedding construction of the demographic information for the episode despite the partially missing modality. When given a new episode snapshot with all data modalities observed, each submodel is applied to the appropriate input data modality, and the unified representation for the new episode snapshot is created.

Preferably, the submodels are advantageously one-way functions in order to ensure security and data privacy. In this way, the original patient information cannot be reconstructed even if both the embeddings and models are available. Consequently, this approach enhances data security and is inherently privacy-preserving.

In contrast to existing approaches, the embedding model 16 according to embodiments of the present invention is able to handle missing data modalities for new episode snapshots based on the episode snapshot graph 40. Further, in contrast to standard methods based on clinical scores like a Simplified Acute Physiology Score (SAPS), the embeddings for an episode snapshot 42 are updated as more information becomes available, according to embodiments of the present invention, and even extends to when new information is available about neighbors. Thus, according to embodiments of the present invention, the episode snapshots 42 change and move in the episode snapshot graph 18.

As another improvement embodiments of the present invention provide over standard approaches, the embedding model 16 does not "reconstruct" or "impute" the missing values. Rather, as discussed above, the submodels are one-way functions. This is an important distinction because imputing-based approaches are inherently not privacy-preserving. In fact, the purpose of imputing-based approaches is that patient data can be reconstructed given the model and embedding.

According to an embodiment of the present invention, each embedding submodel is a one-way function which transforms raw patient data of each episode snapshot into an embedding. One embedding submodel is provided for each data modality 44. For example, there is one submodel for demographics, one submodel for heart rate time series, one submodel for blood oxygen level time series, etc. This allows to use different types of functions for different data modalities. For example, according an embodiment, the form of the function for demographics does not consider time series information, while that for the heart rate time series does. Additionally, using the submodels allows to learn embeddings for the missing data values.

Figure 3:
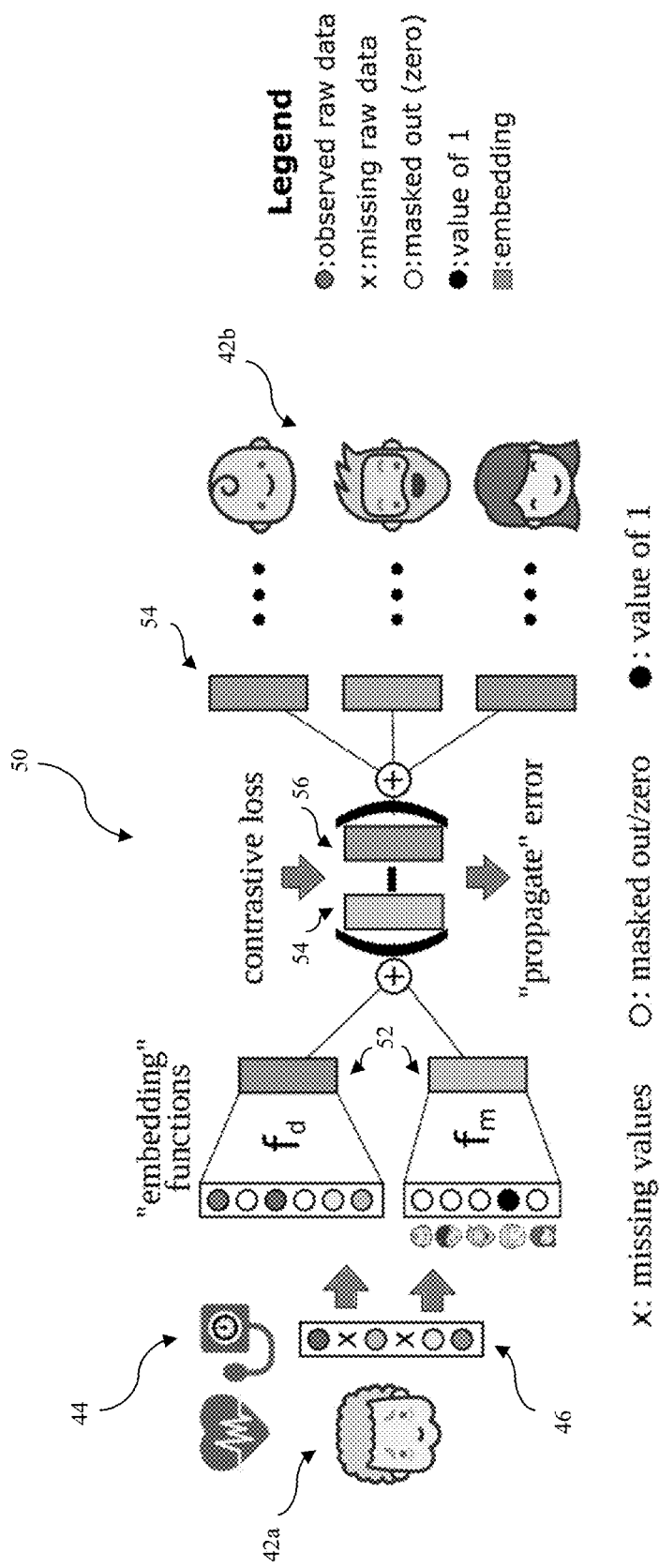
FIG. 3 shows an embedding propagation framework for missing data according to an embodiment of the present invention.

FIG. 3 shows an example of a submodel 50 which learns embeddings 52 for combined heart rate and blood pressure data as a data modality 44, including when some of the raw patient data 46 is missing (indicated by "x"). In the example of FIG. 3, the "grandmother" episode snapshot 42a (on the left) has three neighbor episode snapshots 42b (on the right). The submodel 50 consists of two function, $f_d$ and $f_m$. The first function ($f_d$) embeds all observed raw patient data 46 (indicated by the filled-in circles of different shades), while the second function ($f_m$) gives an embedding for missing raw patient data 46 (indicated by "x") for the episode snapshot 42a. The combination of the two functions (indicated by the "+" on the left of FIG. 3) gives the complete embedding 54 for the episode snapshot 42a. According to an embodiment, element-wise addition is used to combine the embeddings 52 of the episode snapshot 42a (e.g., [4.2]+[1.3]=[5.5]). The intuition is that $f_m$ compensates for the 0s in the input to $f_d$ resulting from the missing data. Thus, the addition of $f_d$ and $f_m$ is still approximately equal to the average of the neighbor embeddings.

The parameters of both functions $f_d$ and $f_m$ are learned with a contrastive loss function. In particular, according to an embodiment, the complete embedding 54 for the modality 44 of the episode snapshot 42a, accounting for both the observed and missing raw patient data 46, is compared with an aggregated embedding 56 of the complete embeddings 54 for the neighbor episode snapshots 42b in the episode snapshot graph (the "+" on the right of FIG. 3). According to an embodiment, the element-wise average is used to aggregate the complete embeddings 54 of the neighbor episode snapshots 42b (e.g., aggregate([1.2], [2.4], [3.6])= [2.4]). This gives rise to a particular type of loss function. The parameters of the submodel 50 are optimized independently so as to minimize this loss, as discussed in further detail below in conjunction with a description of an optimization problem formulation for learning the parameters of the submodels according to an embodiment of the present invention.

The machine learning component 18 is a supervised machine learning component that predicts the patient outcomes of interest, such as the remaining LOS and DD based on the current episode snapshot embedding. Historical outcomes from the episode embedding database 15 are used to train the model. The predictions for some outcomes, such as the LOS of the episode can be made at various levels of granularity. Using LOS as an example, at the finest level, a regression model is used to predict the exact remaining LOS of the episode. A coarser granularity entails prediction of the remaining number of days, while an even more coarse prediction merely predicts whether the duration will be more than a week, which could indicate an extreme outlier. The last two granularities are particularly relevant since most hospitals bill and plan resources on a daily basis, while extreme outliers typically trigger specialized care plans. The fine-grained LOS prediction is a regression problem. The more coarse predictions can be treated as ordinal regression or classification problems. Thus, different existing machine learning models can be used to make the predictions at the different levels of granularity. Advantageously, according to an embodiment of the present invention, the predictions are combined at all granularities to arrive at an estimate of the remaining LOS of the episode.

A second step in the machine learning component 18 uses the embedding, LOS of the episode so far, and estimated remaining LOS to predict the DD. Advantageously, according to an embodiment of the present invention, the machine learning component 18 uses only the embeddings and current LOS, and therefore enhances security and preserves privacy. The machine learning component 18 provides two significant improvements according to embodiments of the present invention: the ability to accurately predict a remaining LOS based on the current LOS, and the ability to accurately predict the DD based on LOS at different levels of granularity.

According to an embodiment of the present invention, the episode embedding database 15 is partitioned into two sets of data. The first includes multiple snapshots of each prior episode including the current episode snapshot embedding, LOS of the episode so far, the known DD, and the true remaining LOS. Thus, the machine learning component 18 can use this partition as training data for the model which predicts the remaining LOS of the episode. This data cannot be used to update the parameters of the embedding model 16. Since only episode embeddings are stored in this partition, it is completely privacy-preserving. Thus, it is advantageously possible according to embodiments of the present invention, for example, for this data to be safely stored in the Cloud. Privacy-sensitive data is stored in a second partition. This data is used to periodically update the parameters of the embedding model 16. Patients can opt-in and allow anonymized versions of their data to be stored in this data in order to improve the system. Since this data includes sensitive information, it is preferably stored in the same computer network as the embedding model 16.

The notification communication system 19 receives the predictions from the machine learning component 18 and sends alerts to the appropriate internal and external facilities of the DDs 30 in order to inform their decision making. For example, if the machine learning component 18 predicts that three patients will be discharged to a specialized nursing facility of the DDs 30, then the machine learning component 18 sends an informative alert to that facility, for example, in the form of an automated electronic notification to a designated electronic communication address of the facility. The notification communication system 18 uses appropriate communications means, such as emails or text messages.

Figure 4:
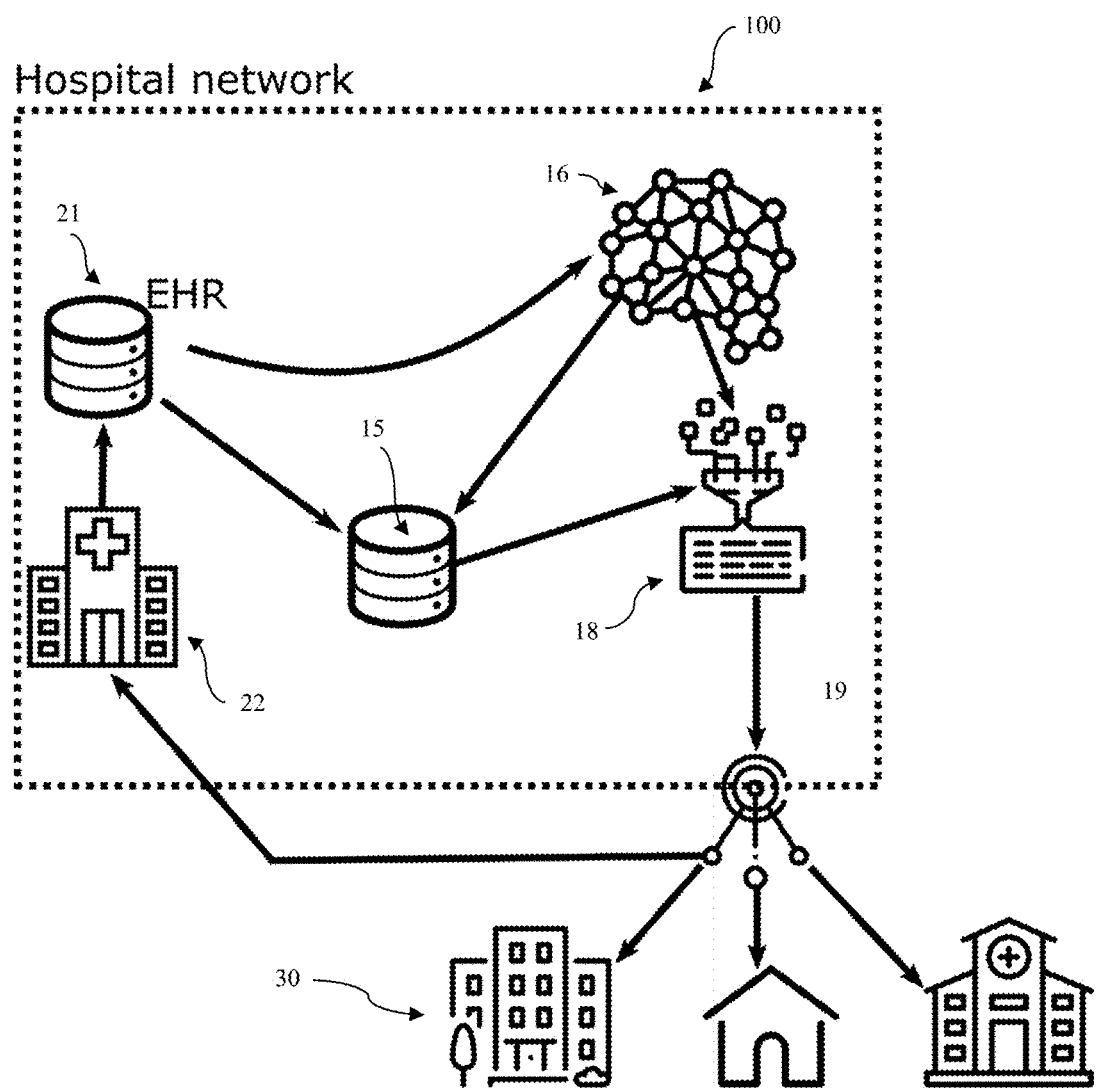
FIG. 4 schematically illustrates an embedded system and method for predicting patient outcomes according to embodiments of the present invention.

According to another embodiment of the present invention schematically illustrated in FIG. 4, the system is an embedded EHR system 100 that is an extension to standard EHR systems and embedded within a caretaker's computing environment (e.g., in a hospital network). This embodiment comprises four main components: an episode embedding database 15 which stores privacy-preserving embeddings of episode snapshots, as well as their outcomes (e.g., LOS and DD), when available; an embedding model 16 which combines observed data of episode snapshots with those from similar episodes to account for missing data in order to create a complete embedding of the episode snapshot; a machine learning component 18 which predicts the outcomes using the embeddings of the episode snapshots; and a notification communication system to 19 alert, for example, the DDs 30, of predicted upcoming patient arrivals.

In contrast to the first embodiment shown in FIG. 1, the embedded EHR system 100 of FIG. 4 is embedded within a particular caretaker's EHR system 21 (e.g., of a hospital 22). While this can be limited to the particular caretaker's available data, the system is more secure and has higher availability rates as a result of being embedded in the existing EHR system 21.

As indicated by the use of same reference symbols for similar components of FIGS. 1 and 4, the core components of the embedded EHR system 100 can be the same as or similar to those in the cloud-based system 10. According to an embodiment, however, there are two primary differences. First, since the embedded EHR system 100 is directly integrated into the EHR system 21, there is no need for a communication interfaces 12a, 12b. Second, again because the embodiment is directly integrated into the EHR system 21, there is no need for different levels of permission. Accordingly, the embedded EHR system 100 does not store episode snapshots, but rather, directly accesses data in the EHR system 21 as needed for the various training and prediction tasks.

Figure 5:
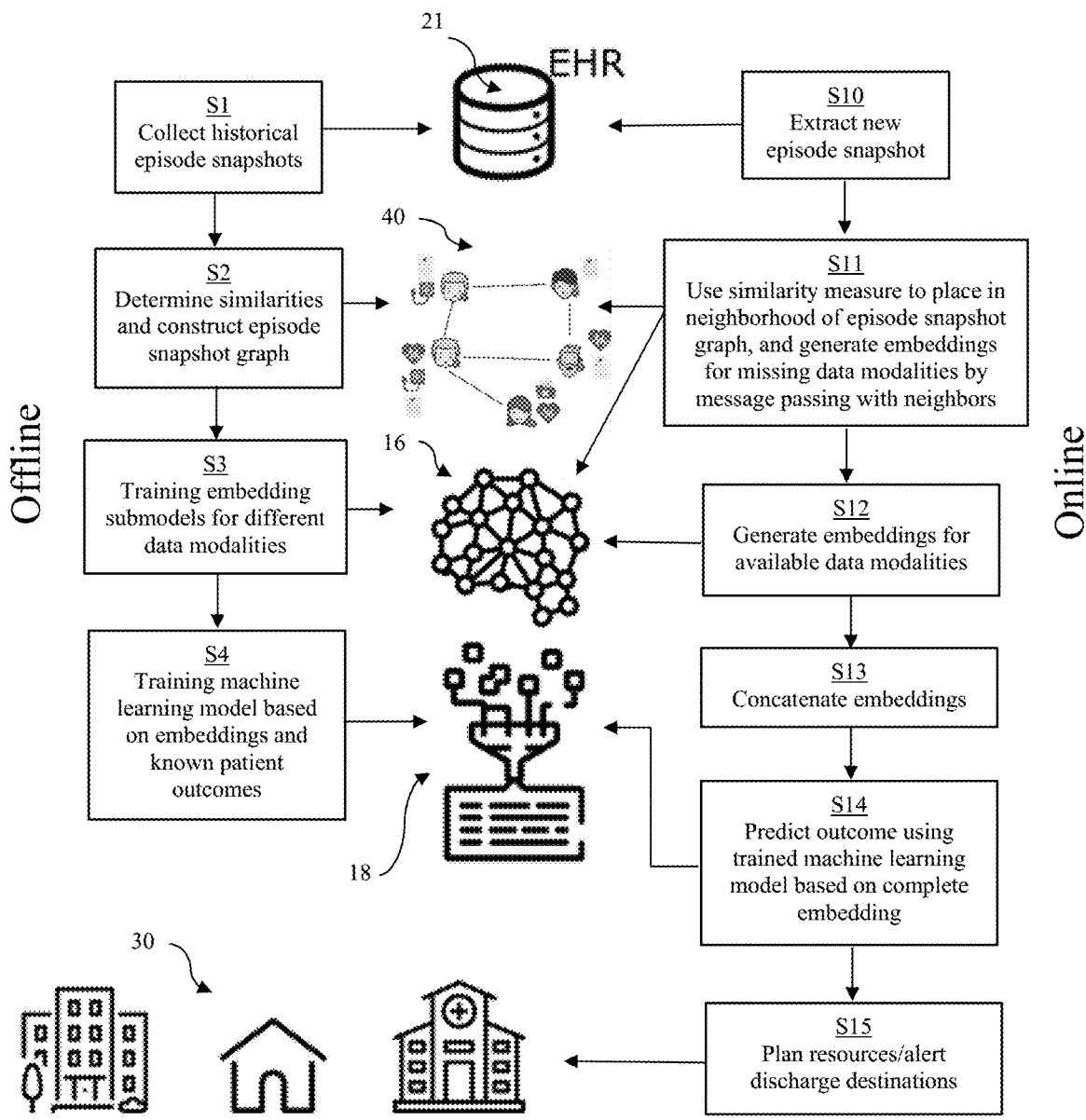
FIG. 5 schematically illustrates the training of embedding and machine learning models and their use to predict a patient outcome according to embodiments of the present invention.

FIG. 5 schematically illustrates an embodiment of a method for training the embedding model 16 and the machine learning model of the machine learning component 18 according to the present invention, along with an embodiment of a method for predicting a patient outcome using the trained embedding and machine learning models according to the present invention. In the training method, which is preferably performed offline, historical episode snapshots and their corresponding patient outcomes (where available) are collected, for example from one or more EHR systems 21 or datasets, in a step S1. In a step S2, the episode snapshot graph 40 is created based on the similarity between episode snapshots defined based on domain knowledge. In a step S3, the episode snapshot graph created in step S2 and data modalities from the historical episode snapshots are used for unsupervised training of an embedding model, in particular submodels for each of the data modalities, for example, as discussed above with reference to FIG. 3. In a step S4, a machine learning model, such as a regression model, of the machine learning component 18 is trained based on the embeddings of the historical episode snapshots and their corresponding patient outcomes (where available). Steps S1-S4 can be repeated as new data becomes available. In the prediction method, which is preferably performed online, a new or current episode snapshot is extracted, for example, from one or more EHR systems 21 in a step S10. For the available data modalities of the new episode snapshot, the respective trained submodels of the embedding model 16 can be used to generate a first embedding in each case in a step S12. For the missing data modalities, a second embedding in each case is generated using neighbors in the episode snapshot graph 40 in a step S11. For this purpose, the new episode snapshot is located in the episode snapshot graph based on the similarity measure defined from domain knowledge, and message passing can be used to generate the embeddings for the missing data modalities in accordance with any of the embodiments discussed herein. In a step S13, the first and second embeddings are concatenated to form a complete embedding for the new episode snapshot. This complete embedding is used in a step S14 as input to the trained machine learning model of the machine learning component 18, which predicts the patient outcome. Then, in step S15, the predicted patient outcome including, for example, LOS and DD is used to plan hospital and healthcare resources, for scheduling purposes and/or for alerting respective DDs in advance of a predicted discharge to that location at a predicated time.

Advantages and improvements provided by embodiments of the present invention include, for example:
1) Generating embeddings for missing data modalities in a time-dependent manner based on neighbors in the episode snapshot graph and an embedding model trained to account for the missing data modalities.
2) Predicting patient outcomes using the embeddings, in particular at multiple granularities according to an embodiment.
3) Learning embeddings of episode snapshots based on multiple, separate modalities of data, including time series, text, demographics, etc.
4) Using these learned multi-modal embeddings learn embeddings for missing data modalities during training.
5) Learning embeddings in an unsupervised manner, according to an embodiment, which advantageously does not require many episode snapshots labeled with their outcomes to still have high-quality predictions.
6) Generating embeddings of episodes based on their current snapshots regardless of the modalities of data which have been collected. This has been demonstrated statistically to significantly improve LOS predictions relative to existing approaches, and also results in improved accuracy of the DD predictions.
7) The embedding model learns one-way functions, which advantageously provides that it is not possible to recreate the original patient data even if both the model and patient embeddings are available, thereby enhancing data security and patient privacy.

According to an embodiment, the present invention provides a method for predicting remaining LOS of an episode and DD of a patient from multi-modal data, which is acquired through the course of the episode and has missing data, the method comprising:

1) Generating an embedding for each observed data modality, based on what has been observed so far, of the current episode snapshot using the submodel functions.
2) Summarizing each data modality of similar episode snapshots ("neighbors") with an aggregated embedding by aggregating the output of the submodel functions.
3) Combining the embeddings of the current episode with those from neighbors to create a complete embedding for the current episode.
4) Predicting the remaining LOS of the episode with the complete embedding by considering multiple levels of granularity.
5) Predicting the DD using the complete episode embedding.
6) Alerting the DDs of expected patient arrivals.

According to another embodiment, the present invention provides a method for predicting remaining LOS of an episode and the DD of a patient from multi-modal data, which is acquired through the course of the episode and has missing data, the method comprising:
1) Generating a complete embedding for the current episode by combining embeddings of observed data for the current episode with summarized embeddings of all data from neighbors; each data modality is associated with a submodel which performs the embedding for that modality.
2) Predicting the remaining LOS of the episode based on the complete embedding using a supervised machine learning algorithm.
3) Predicting the DD of the episode using the complete embedding.
4) Alerting the DDs of expected patient arrivals.

According to a further embodiment, the present invention provides a method for predicting remaining LOS of an episode and the DD of a patient from multi-modal data, which is acquired through the course of the episode and has missing data, the method comprising:
1) Training an embedding model, preferably unsupervised, based on historical episode snapshots.
2) Training a supervised machine learning model to predict patient outcomes based on embeddings of the episode snapshots and corresponding historical patient outcomes of the episodes.
3) Extracting episode snapshots from an EHR system.
4) Generating a complete embedding for a current episode snapshot by combining: (1) for observed data in the episode snapshot, embeddings from the submodels; and (2) for missing data, aggregated embeddings of neighbors in the episode snapshot graph (e.g., the average taken in Equation 4 below), each data modality being associated with a submodel which performs the embedding for that modality.
5) Predicting the patient outcome for the current episode snapshot, preferably at multiple levels of granularity, based on the complete embedding using a supervised machine learning component.

Steps 1) and 2) of the above method can be performed offline and/or as a separate method for training the embedding model on historical data. Steps 3)-5) of the above method can be performed online and/or as a separate method for predicting the outcome for a new patient.

In the following, an embodiment of the present invention is described in further detail. This embodiment uses a particular type of message-passing for graph representation learning. In representation learning for graph-structured data, edges in a graph connect instances deemed similar in some way and a message passing scheme is used to learn embeddings of the data modalities associated with each instance. While there are several message-passing approaches to graph representation learning which have been proposed, one particularly advantageous embodiment of the present invention uses a message-passing approach referred to as embedding propagation (EP), a method that is both unsupervised and learns a representation specific to each data modality (see Garcia-Duran, A., et al., "Learning graph representations with embedding propagation," in Advances in Neural Information Processing, (2017)). An embodiment of the present invention recognizes that EP has several characteristics that make it well-suited for the learning from medical records setting. First, it provides a method for learning and combining representations of the various data modalities typically found in EHRs. For instance, it is possible to simultaneously learn embeddings of free text notes and to combine these with embeddings learned for the measurement time series data. Second, due to its unsupervised reconstruction loss, it allows to learn a vector representation for every data modality and every patient, even if that particular data modality is not observed at all for some of the patients. Third, since EP learns in a first step embeddings for each data modality independently, the resulting predictions are more interpretable as it is possible to distinguish between the influence of these independently learned modality embeddings on the predictions. For instance, it is possible to assess the influence of the free text data and the time series data. Intuitively, EP learns data embeddings such that embeddings of nodes close in the graph, that is, nodes similar in one or several ways, are more similar to each other than those of nodes far away in the graph. If desired, the embeddings can then be used in a traditional downstream machine learning task. In the context of EHRs, patients are modeled as nodes in the graph and similarity relationships between patients are modeled with edges.

According to an embodiment, the present invention extends the EP framework to account for missing data. In particular, for each data modality, two embeddings are learned for each patient; the first embedding carries information about the observed data, while the second embedding is learned for missing data. Learning an explicit embedding of missing data within the graph-based learning framework has the advantage of propagating embeddings of missing data throughout the graph such that these embeddings are also informed by embeddings of neighboring patients. Combining these learned feature embeddings gives a complete embedding for downstream tasks.

A recently-introduced benchmark based on the medical information mart for intensive care III (MIMIC-III) dataset was used to evaluate the proposed approach according to embodiments of the present invention and show that it is competitive with existing approaches when using a single data modality, in particular, numeric time series observations. After augmenting the data with additional data modalities, including free text from physicians' notes and categorical demographic information, it was demonstrated that the proposed approach outperforms the existing approaches on LOS and DD prediction. The MIMIC-III dataset can be used as training data to select parameters of the various embedding submodels and the machine learning component model. Another public dataset which could be used for training according to an embodiment is eICU.

The original benchmark dataset includes seventeen time series variables, sampled at varying frequencies and many of which are missing for some patients. Further, each admission includes a "subject_id" and "episode" which link it back to the complete MIMIC-III dataset. Foreign keys were used to augment the time series variables with text (from the "note_events" table) and demographic (from the "admissions" and "patients" tables) data. In both cases, it was ensured to only use data available at the time of prediction. For example, the data under "discharge summaries" was never used to predict mortality.

In a preprocessing step, features were extracted from the time series data. Seven sets of observations were created from each time series (the entire sequence, and the first and last 10%, 25% and 50% segments of the sequence). Nine features were then calculated for each segment (count, minimum, maximum, mean, standard deviation, skew, kurtosis, median, and max absolute deviation). Thus, in total, for each time series, there are 7×9=63 features. This number of features is larger than earlier works extracting features from the MIMIC-III dataset and includes median and max absolute deviation features which are robust against outliers. Missing values were replaced with the mean of the respective feature. Finally, all observations were standardized such that each feature has a mean of 0 and a variance of 1 across all patients in the training set.

The text notes were first partitioned based on their "category" into six types: nursing, radiology, respitory, ecg, echo and other. Each note was then converted into a bag of words representation. All words which appear less than 0.1% or more than 90% of the notes were discarded. The concatenated notes for each category were used as the text observations for each patient. Accordingly, each patient had six bag-of-word text features, one for each type.

Further, we extract admission and demographic information about each episode were extracted from the respective tables of the MIMIC-III dataset. In particular, the "admission_type" was collected (e.g., urgent, elective, etc.) along with the "admission_location" (e.g., emergency room) and the "diagnosis" (e.g., a preliminary, free text diagnosis usually assigned by the admitting clinician and does not use a systematic ontology) about the admission. Each of these three fields contains text. Also collected were the patient's ethnicity, gender, age, insurance and marital status.

Three prediction tasks were performed to predict: in-hospital mortality (mort), LOS and DD. In all cases, the predictions were made 2 days after admission to the ICU. The same semantics for the starting time of an episode was used as in previous works on the MIMIC-III dataset. For mort, this is exactly the same problem in the original benchmarks. Although DD prediction has been considered in several medical studies (see, e.g., Stecker, M. et al., "Predictive model of length of stay and discharge destination in neuroscience admissions," Surgical Neurology International (2017), the entire contents of which is hereby incorporated by reference herein), the approaches used have relied on traditional clinical scores such as the functional independence measure (FIM) or Berg balance scores. Prior approaches for DD prediction have not considered machine learning. In contrast to the binary mort classification task, the DD prediction task is a multiclass classification problem. In particular, the set of patients in the MIMIC-III in this study had six discharge destinations after grouping. Conceptually, DD can be considered to be a more fine-grained proxy for the eventual patient outcome compared to mort.

The general learning framework of EP proceeds in two separate steps. In the following, the term "attribute" is used to refer to a particular node feature or raw patient data and the term "representation" can also be referred to as an embedding, as in the embodiments described above. Moreover, an "attribute type" is used to refer to a data modality and represents either one node attribute or a set of node attributes grouped together. In a first step, EP learns a vector representation for every attribute type by passing messages along the edges of the input graph. In the context of learning from EHRs, for example, one attribute type consists of time series data recorded for ICU patients. The attribute types used included (1) a group of time-series data from ICU measurements; (2) words of free-text notes; and (3) a group of categorical features of demographic data. In a second step, EP learns patient representations by combining the previous learned attribute type representations. For instance, the method would combine the representation learned for the doctors' notes with the representation learned for the time series data. These combined node representations are then used in the downstream prediction tasks.

Each attribute type i is associated with a domain $D_i$ of possible values. For instance, an attribute type consisting of N numerical attributes has the domain $\mathbb{R}^N$ and an attribute type modeling text data has the domain $\mathbb{R}^{|T|}$ where T is the vocabulary. For each attribute type, a suitable encoding function f is chosen. This encoding function f is parameterized and maps every $x_i \in D_i$ to its vector representation $x_i' \in \mathbb{R}^{d_i}$ that is, $x_i' = f_i(x_i)$. These encoding functions have to be differentiable to update their parameters during learning.

The functions $l_i: V \to 2^{D_i}$ map every vertex v in the graph to a (possibly empty) set of vectors $x_i \in D$. The function $l(v) = \cup_i l_i(v)$ is written for the set of all vectors of attribute type i associated with vertex v. Moreover, the function $l_i(N(v)) = \{l_i(u) | u \in N(v)\}$ is written for the multiset of labels of type i associated with the neighbors of vertex v.

EP learns a vector representation for each of the attribute types of the problem. The following two key concepts help to formalize the EP learning framework:

$h_i(v)$ is written to denote the current vector representation of attribute type i for node v. It is computed as follows:

$$h_i(v) = g_i(\{f_i(x) | x \in l_i(v)\})$$ (Equation 1)

$\widetilde{h}_i(v)$ is written to denote the reconstruction of the representation of attribute type i for node v. $\widetilde{h}_i(v)$ is computed from the attribute type representations of v's neighbors in the graph. It is computed as follows:

$$\widetilde{h}_i(v) = \widetilde{g}_i(\{f_i(x) | x \in l_i(N(v))\}),$$ (Equation 2)

where $g_i$ and $\widetilde{g}_i$ are aggregation functions that map a multiset of of $d_i$-dimensional embeddings to a single $d_i$-dimensional embedding. These aggregation functions can be parameterized but are often parameter-free aggregation functions such as the element-wise average of maximum.

The core idea of EP is to make the attribute type representation and its reconstruction similar for each attribute type and each node in the graph. In other words, EP learns attribute type representations such that the distance between $h_i(v)$ and $\widetilde{h}_i(v)$ is small. More formally, for all attribute types EP minimizes the following loss:

$$\mathcal{L}_i = \Sigma_{v \in V} \Sigma_{u \in V \setminus \{v\}} [\gamma + d_i(\widetilde{h}_i(v), h_i(v)) - d_i(\widetilde{h}_i(v), h_i(u))]^+,$$ (Equation 3)

where $d_i$ is the Euclidean distance, $[x]_+$ is the positive part of x, and $\gamma > 0$ is a margin hyperparameter.

The margin-based loss defined in Equation 3 updates the parameters (i.e., the embedding functions and functions $g_i$ and $\widetilde{g}_i$ in case they are chosen to be parametric) if the distance between $h_i(v)$ and $\widetilde{h}_i(v)$ plus a margin is not smaller than the distance between $h_i(u)$ and $\widetilde{h}_i(v)$, with u being a randomly sampled node different from v. Intuitively, for each patient node v and attribute type i, the vector representation reconstructed from the embeddings of patient nodes neighboring v are learned to be more similar to the embedding of attribute type i for v than to the embedding of attribute type i of a random patient node in the graph.

The generic working of the label representation learning stage is as follows: In each propagation step, for each node v in the graph, and for each attribute type i, the embeddings $\widetilde{h}_i(v)$, $h_i(v)$ and $h_i(u)$ are computed. Then, a node u is sampled uniformly at random from the set of all nodes and for every v in each learning iteration. Finally, parameters of the model are updated based on the loss defined in Equation 3.

For all attribute types the function $f_i$ is chosen to be a linear projection. Hence, it is provided that $x' = (x) = x^T W_i$. Moreover, it is chosen:

$$g_i(\mathcal{H}) = \widetilde{g}_i(\mathcal{H}) = \frac{1}{|\mathcal{H}|} \sum_{h \in \mathcal{H}} h$$ (Equation 4)

for attribute types i and sets of embedding vectors $\mathcal{H}$. While the learned attribute label embeddings are learned via a locally linear transformation, the method results in a non-linear feature transformation due to the use of the affinity graph and the non-iid (independent and identically distributed) nature of the patients.

Two characteristics of EP make it suitable for the problem of learning representation for missing data according to embodiments of the present invention. First, it supports an arbitrary number of attribute types and one can learn missing data representations tailored to attribute types. Second, EP's learning principle is based on reconstructing each node's embedding from neighboring nodes' embeddings and this makes it highly suitable for settings wherein a number of nodes have missing data. Due to the unsupervised loss function used in EP, it is also highly suitable for the semi-supervised learning setting where class labels are missing for a fraction of nodes. During training, EP learns how to reconstruct the missing data representation based on a contrastive loss between representations of existing labels, or embeddings of episode snapshots (see FIG. 3), and, therefore, can learn how to reconstruct a representation when data is missing.

For every attribute type i and for every node $v \in V = \{1, \ldots, |V|\}$ of the graph, there is an input feature vector x. Based on this vector, two feature vectors are created. The first feature vector $x_1$ is identical to x except that all missing values are masked out. The second feature vector $x_2 \in \mathbb{R}^{|V|}$ is either (1) all zeros if there are no missing attribute values for attribute type i or (2) all zeros except for the position v which is set to 1. The vector $x_2$ indicates whether data is missing and learns a latent representation for nodes with missing data. These two vectors are then fed into two encoding functions $f_i^1$ and $f_i^2$ whose parameters are learned independently from each other. For each input, the output vectors of the encoding functions are added element-wise and the resulting vector used in the margin-based contrastive loss function. FIG. 3 illustrates the approach to learning separate representations for observed and missing attribute labels. Since the contrastive loss compares representations that are computed both based on missing and observed data, the two representations influence each other. If for some node v and attribute type i there is missing data, the representation of that missing data is influenced by the representations of observed and missing data of attribute type i by neighboring nodes.

Once the learning of attribute type representations has finished, EP computes a vector representation for each patient vertex v from the vector representations of v's attribute types. In this embodiment, the function r computes the concatenation of the attribute type representations:

$$v = \text{concat}[h_1(v), \ldots, h_k(v)] \qquad \text{(Equation 5)}$$

Since missing data has been modeled explicitly, the latent representations $h_i$ (v) exist for every node in the graph and every attribute type i.

Hyperparameters: 200 iterations of training were used with mini-batches of size 256. All label types (data modalities) were embedded in a 32-dimensional space. It was set the margin $\gamma=5$, and the EP optimization problem was solved using Adam (an existing adaptive learning rate optimization algorithm) with a learning rate of 1e-3. EP was implemented in Keras (an open source neural network library) using TensorFlow as the backend. All experiments were run on commodity hardware with 32 or 128 GB RAM, up to four quad-core 2.8 GHz CPU, and a TitanX GPU. The computing cluster was in a shared environment, so running times were not reported. In all cases, though, the running times were modest, ranging from a few minutes up to about an hour for the longest experiments.

Baseline models: It has been shown that linear models perform admirably compared to much more sophisticated methods on these and similar benchmark problems. Thus, (multi-class) logistic regression was used as a baseline for mort and DD. Likewise, ridge regression (also known as linear least squares with L2 regularization) was used as the baseline for LOS. Both implementations are from scikit-learn (a free software machine learning library). All hyperparameters were selected based on cross-validation.

Construction of the episode snapshot graph: An integral component of EP is the input graph; it gives a mechanism to capture domain knowledge about the similarity of the nodes to which traditional machine learning approaches do not have access. In this embodiment, since the goal is always to make a prediction about the outcome of an episode, each node in the graph corresponds to an episode.

As described above, the admission type, location, and initial diagnosis are extracted about each episode. The construction of the graph is based on the text from these fields. In particular, the three fields are concatenated to form a "document" for each episode. According to an embodiment of the present invention, the document is a brief textual description about the admission, such as "emergency transfer from hosp/extram interior myocardial infarction." Next, fastText (an existing library for text classification and representation learning) is used to learn custom word embeddings via skip-grams from this corpus. These are then used to calculate a single embedding (or a "sentence vector") for the document, or the textual description, for each episode. The similarity between two episodes is then defined as i and j as:

$$s_{i,j} = \exp{-d_{i,j}} \qquad \text{(Equation 6)}$$

where $d_{i,j}$ is the Euclidean distance between the respective sentence embeddings. Finally, all pairs of episodes are connected for which $s_{i,j} > 0.9$. This threshold is empirically selected since it gives a graph density similar to those found in commonly-used benchmarks like citation networks.

Data partitioning: The MIMIC-III benchmark datasets are provided with a standard training and testing set split of episodes for their mort benchmark problem. In total, the training set includes 17,869 episodes, while the testing set includes 3,233 episodes. While modest in comparison to some datasets considered in the machine learning community, this dataset is huge compared to many datasets presented in the medical literature. Thus, the ability to generalize to the test set when outcome information is available for smaller numbers of training episodes was also considered. In particular, subsets of varying size were provided and only the labels for those episodes were observed. As described above, EP can still take advantage of the unlabeled episodes, for which the outcomes like LoS or DD are not known. On the other hand, completely supervised methods can only use the episodes with labels. The predictions were always made 48 hours after admission and it was ensured that the learning only considers information that would be available in such a realistic scenario.

Evaluation metrics: Standard metrics were used for evaluation. In particular, the area under the receiver operating characteristic curve (AuROC) was used to evaluate mort, mean absolute error (MSE) was used to evaluate LoS, and the multi-class generalization of AuROC (mc-AuROC) was used to evaluate DD.

Figure 6:
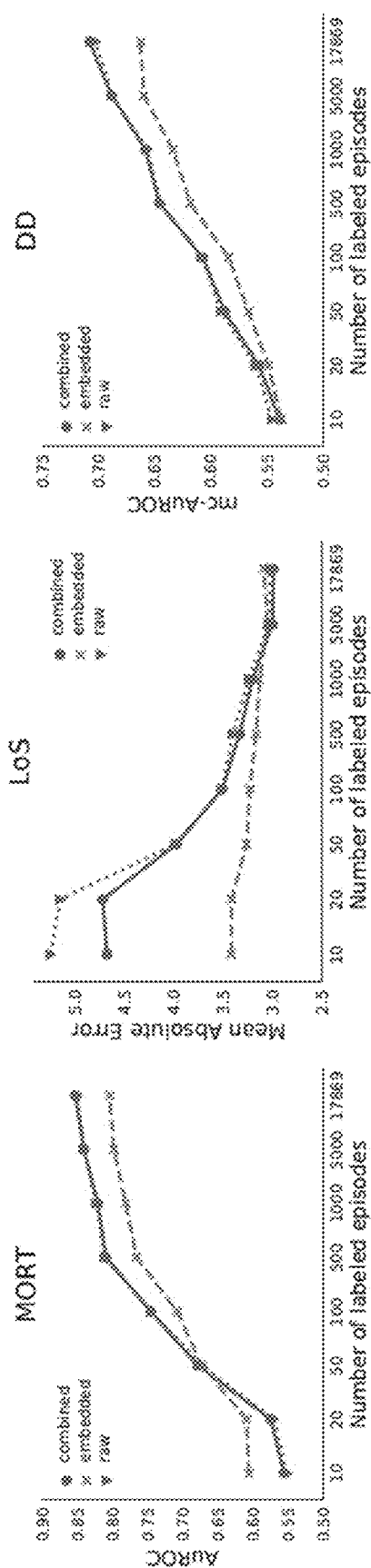
FIG. 6 is a graphical comparison of performance for raw features, embedded episode embeddings and combined features for training a logistic regression model using a single time-series modality as input.

First, the impact of learning embeddings on only the time series data present in the original benchmarks and using that in downstream prediction was considered. FIG. 6 compares the performance of the "raw" baseline (using just the hand-crafted features) compared to a first learning representations of the time series features using EP (labelled as "embedded" in FIGS. 5 and 6). A third strategy in which the original features are combined with the representations learned by EP by concatenating the two feature vectors for each episode is also shown (labelled as "combined" in FIGS. 6 and 7). The respective performance of using only the "raw" features, only the "embedded" features and the "combined" features for training a logistic regression model are shown in FIG. 6 using time series measurements as a single data modality input. The x-axis shows the number of labeled training episodes (out of the total of 17,869 episodes in the full training set). 20 random samples of the various subset sizes were evaluated for each feature representation. The markers give the mean performance on the entire test set, and the error bars show the standard deviation.

As shown in FIG. 6, the embeddings are particularly helpful in small-data scenarios for mort and LOS. The embeddings are particularly well-suited for LOS. Indeed, this is the only task in this single data modality setting in which "combined" meaningfully differs from "raw". Thus, it is seen that even with only a single data modality, embeddings which handle missing data still improve performance.

Multi-modal data analysis: The analysis was then extended to multi-modal data. As described above, EP was used to learn embeddings for each of the four data modalities (time series features, text notes, demographics, and episode identity within the graph) independently. The final representation for the episode is the concatenation of all modality embeddings. For the baseline, standard text and categorical variable preprocessing were used. In particular, the term-frequency inverse document-frequency for each note type was computed, and these were used as features. The (categorical) demographic variables were one-hot encoded, and then treated as a bag of words. The graph for EP was constructed using additional information about the episode admission, as discussed above. In order to ensure all approaches have access to the same data, the data was also encoded as categorical variables and included with the demographic information for the "raw" baseline.

Figure 7:
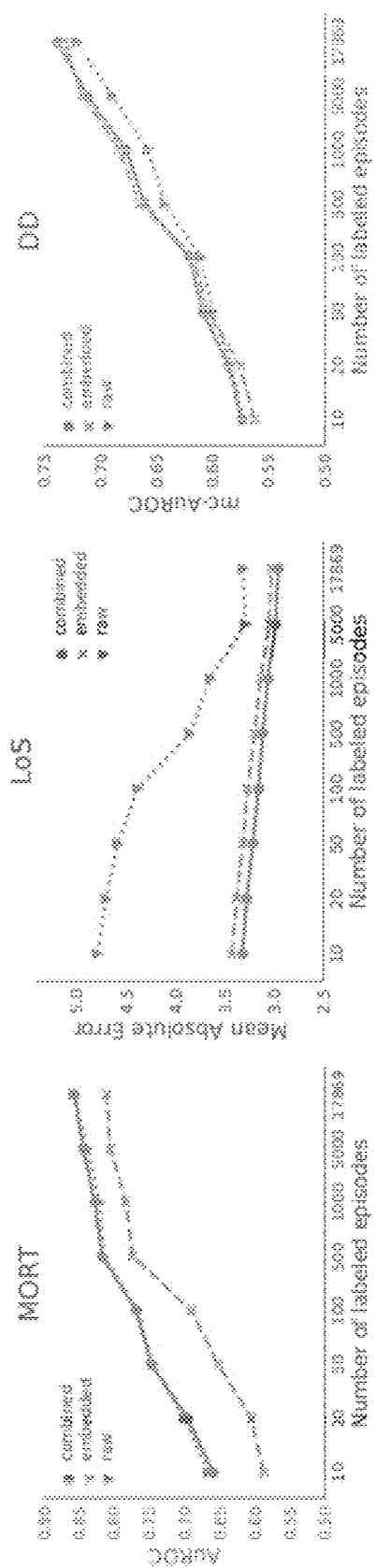
FIG. 7 is a graphical comparison of the performance of the three strategies of FIG. 6 using four data modalities as input.

FIG. 7 shows the performance of the respective strategies after adding the additional data modalities (i.e., all four data modalities). Relative to their performance in the single-modality setting of FIG. 6, the performance for all three representations improves across nearly all tasks and observed episode subsets. For mort, as in the single-modality case, "embedded" performs worse than using only the hand-crafted features. However, combining the embeddings with the raw features does no harm, and "combined" and "raw" perform virtually identically for the mort prediction task. The "combined" representation benefits significantly from the additional data modalities on the LOS prediction task. Indeed, it outperforms both "raw" and "embedded" across all subsample sizes. In this task, it seems as though "combined" is effectively using information from both "raw" and "embedded" rather than simply learning to use the best, as seems the case in many of the other settings. Finally, all of the representations show significant improvement in the DD task when the additional modalities are available. Both "embedded" and "combined" significantly outperform "raw" for the DD task with a significant sample size.

According to other embodiments, different prediction tasks, such as predicting the computational phenotype, could be applied using the embedding model. Likewise, the data modalities can include medications, procedures, treatments and the like that occur during the course of an episode, the embeddings of which can also be updated during the episode. Moreover, other sources of data other than EHR's can be used to extract the relevant data modalities for the relevant prediction task.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for predicting a patient outcome from a caretaker episode, the method comprising:
    receiving a current episode snapshot of the caretaker episode comprising multi-modal data of the patient from an electronic health records (EHR) system, the multi-modal data including one or more available data modalities and one or more missing data modalities;
    applying the multi-modal data as input to an embedding model having a submodel for each of the data modalities;
    generating a first embedding for each of the available data modalities using a respective one of the submodels;
    generating a second embedding for each of the missing data modalities using corresponding embeddings of neighbors in an episode snapshot graph which connects the current episode snapshot to other historical episode snapshots based on a similarity measure;
    combining the first and second embeddings to obtain a complete embedding for the current episode snapshot; and
    predicting the patient outcome based on the complete embedding for the current episode snapshot using a machine learning component which has been trained using patient outcomes of the historical episode snapshots.

2. The method according to claim 1, wherein the patient outcome includes a remaining length of stay (LOS) and a discharge destination (DD), and wherein the DD is predicted using the predicted LOS.

3. The method according to claim 2, further comprising alerting the predicted DD of the predicted patient outcome.

4. The method according to claim 2, wherein the remaining LOS prediction is made by combining predictions at different levels of granularity including a first prediction at a finer granularity made using a regression model and at least one second prediction at a coarser granularity made using an ordinal regression or classification model.

5. The method according to claim 1, wherein the embedding model is an unsupervised embedding model trained based on the historical episode snapshots.

6. The method according to claim 1, wherein the machine learning component includes a supervised machine learning model trained to predict the patient outcome based on embeddings of the episode snapshots and outcomes of the historical episode snapshots.

7. The method according to claim 1, wherein each of the submodels of the embedding model is a one-way function whose parameters are learned with a contrastive loss function comparing an embedding of a respective one of the data modalities, accounting for observed and missing values, with an aggregated embedding of embeddings of the respective one of the data modalities from the neighbors in the episode snapshot graph.

8. The method according to claim 1, wherein the multi-modal data originates from different EHR systems.

9. The method according to claim 1, wherein the multi-modal data includes at least time series measurements, free text notes and demographic information.

10. A system for predicting a patient outcome from a caretaker episode, the system comprising at least one server operable to receive patient raw data for the caretaker episode from at least one electronic health records (EHR) system, the at least one server having one or more computational processors which, alone or in combination, are configured to provide for execution of a method comprising:
    receiving a current episode snapshot of the caretaker episode comprising multi-modal data of the patient from the at least one EHR system, the multi-modal data including one or more available data modalities and one or more missing data modalities;
    applying the multi-modal data as input to an embedding model having a submodel for each of the data modalities;

generating a first embedding for each of the available data modalities using a respective one of the submodels;

generating a second embedding for each of the missing data modalities using corresponding embeddings of neighbors in an episode snapshot graph which connects the current episode snapshot to other historical episode snapshots based on a similarity measure;

combining the first and second embeddings to obtain a complete embedding for the current episode snapshot; and predicting the patient outcome based on the complete embedding for the current episode snapshot using a machine learning component which has been trained using patient outcomes of the historical episode snapshots.

11. The system according to claim 10, wherein the at least one server is located in the Cloud and is configured to receive the patient raw data from different EHR systems by secure communication with respective communication interfaces within the different EHR systems.

12. The system according to claim 10, wherein the at least one server is embedded within the at least one EHR system.

13. The system according to claim 10, further comprising an episode snapshot database storing at least a portion of the episode snapshots, and an episode embedding database storing the complete embeddings of at least a portion of the episode snapshots and at least a portion of known outcomes of the episode snapshots.

14. The system according to claim 10, wherein the patient outcome includes a remaining length of stay (LOS) and a discharge destination (DD), the system further comprising a notification communication system configured to alert the predicted DD about the predicted patient outcome.

15. A tangible, non-transitory computer-readable medium having instructions thereon which, upon execution by one or more processors, provide for execution of a method comprising:

receiving a current episode snapshot of the caretaker episode comprising multi-modal data of the patient from an electronic health records (EHR) system, the multi-modal data including one or more available data modalities and one or more missing data modalities;

applying the multi-modal data as input to an embedding model having a submodel for each of the data modalities;

generating a first embedding for each of the available data modalities using a respective one of the submodels;

generating a second embedding for each of the missing data modalities using corresponding embeddings of neighbors in an episode snapshot graph which connects the current episode snapshot to other historical episode snapshots based on a similarity measure;

combining the first and second embeddings to obtain a complete embedding for the current episode snapshot; and predicting the patient outcome based on the complete embedding for the current episode snapshot using a machine learning component which has been trained using patient outcomes of the historical episode snapshots.

* * * * *